United States Patent [19]
Nishimura et al.

[11] Patent Number: 6,047,560
[45] Date of Patent: Apr. 11, 2000

[54] PROCESS FOR SEPARATING PENTAFLUOROETHANE AND 1,1,1-TRIFLUOROETHANE

[75] Inventors: Atsuo Nishimura; Toshio Nagayasu; Reiji Takahashi, all of Kanagawa, Japan

[73] Assignee: Showa Denko K.K., Tokyo, Japan

[21] Appl. No.: 09/041,023

[22] Filed: Mar. 12, 1998

Related U.S. Application Data

[60] Provisional application No. 60/053,170, Jul. 18, 1997.

[30] Foreign Application Priority Data

Mar. 12, 1997 [JP] Japan ..................................... 9-058103

[51] Int. Cl.[7] ....................................................... F25J 1/00

[52] U.S. Cl. .................. 62/617; 62/918; 203/44; 570/178

[58] Field of Search ..................... 62/617, 918; 570/178; 203/44, 45

[56] References Cited

U.S. PATENT DOCUMENTS

| | | | |
|---|---|---|---|
| 3,282,801 | 11/1966 | Wiist | 62/918 X |
| 3,732,150 | 5/1973 | Bailey | 203/44 |
| 5,830,325 | 11/1998 | Mahler et al. | 570/178 X |

*Primary Examiner*—Ronald Capossela
*Attorney, Agent, or Firm*—Sughrue, Mion, Zinn Macpeak & Seas, PLLC

[57] ABSTRACT

A process for separating pentafluoroethane and 1,1,1-trifluoroethane, which comprises extraction distilling a mixed fluid comprising pentafluoroethane and 1,1,1-trifluoroethane in the presence of at least one extracting agent selected from the group consisting of esters and ketones each having a standard boiling point of from −10° C. to 100° C. Also disclosed is a process for separating pentafluoroethane, 1,1,1-trifluoroethane and chloropentafluoroethane, which comprises extraction distilling a mixed fluid comprising pentafluoroethane, 1,1,1-trifluoroethane and chloropentafluoroethane in the presence of at least one extracting agent selected from the group consisting of esters and ketones each having a standard boiling point of from −10° C. to 100° C.

19 Claims, No Drawings

PROCESS FOR SEPARATING PENTAFLUOROETHANE AND 1,1,1-TRIFLUOROETHANE

CROSS REFERENCE TO RELATED APPLICATIONS

This application is an application filed under 35 U.S.C. §111(a) claiming benefit pursuant to 35 U.S.C. §119(e) (i) of the filing date of the Provisional Application 60/053,170 filed Jul. 18, 1997 pursuant to 35 U.S.C. §111(b).

FIELD OF THE INVENTION

The present invention related to a process for efficiently separating the respective constituent components of a mixed fluid comprising pentafluoroethane (hereinafter referred to as "HFC-125") and 1,1,1-trifluoroethane (hereinafter referred to "HFC-143a") or a mixed fluid comprising HFC-124, HFC-143a and chloropentafluoroethane (hereinafter referred to as "CFC-115").

BACKGROUND OF THE INVENTION

A distillation method is not commonly used for separating a fluid mixture into its respective constituent components.

However, because HFC-125 and HFC-143a have such close standard boiling points of −48.5° C. and −47.2° C. and because the specific volatility of HFC-143a relative to HFC-125 is close to 1, a mixed fluid comprising HFC-125 and HFC-143a is known to form an azeotropic composition. Accordingly, it is very difficult to separate these components using a common distillation method alone.

Also, in the case of CFC-115 having a standard boiling point of −38.7° C., its specific volatility relative to HFC-125 is also close to 1. Accordingly, a mixed fluid comprising HFC-125 and CFC-115 is know to form an azeotropic composition and is therefore very difficult to separate using a general distillation method.

To cope with these problems, an extraction distillation method can be applied, in which an extracting reagent is added to a fluid mixture forming an azeotropic composition as a third component having a standard boiling point different from the standard boiling points of the other components.

With respect to the separation of a mixed fluid having an azeotropic composition comprising HFC-125 and HFC-143a hitherto proposed, U.S. Pat. No. 3,732,150 discloses an azeotropic distillation method which comprises adding ammonia to a mixed fluid to form an azeotropic comprising HFC-143a and ammonia to thereby allow for the separation of HFC-125.

Furthermore, the present inventors have proposed in JP-A-9-12487 (the term "JP-A" as used herein means an "unexamined published Japanese patent application") an extraction distillation method using at least one extracting reagent selected from carbon chlorides and chlorinated hydrocarbons each having 1 and 2 carbon atoms.

With respect to the separation of an azeotropic mixed fluid having an azeotropic composition comprising HFC-125 and CFC-115 hitherto proposed, U.S. Pat. No. 5,087,329 discloses an extraction distillation method using a carbon fluoride having from 1 to 4 carbon atoms or a hydrogen and/or chlorine adduct thereof.

Furthermore, the present inventors have proposed in JP-A-7-133240 an extraction distillation method as applied to a mixed fluid comprising HFC-125 and CFC-115 using an extracting agent selected from paraffinic hydrocarbons, alcohols, ethers, esters and ketones each having a standard boiling point of from −10° C. to 100° C. Also, the present inventors have proposed in JP-A-8-143486 an extraction distillation method using an extracting agent selected from carbon chlorides and chlorinated hydrocarbons each having 1 or 2 carbon atoms.

However, the extracting reagents used in these conventional techniques for separating a mixed fluid comprising HFC-125 and HFC-143a are not as effective as desired. Moreover, ammonia used as an azeotropic agent is toxic and dangerous to handle.

Furthermore, no publication hitherto describes a technique for separating a mixed fluid comprising HFC-125, HFC-143a and CFC-115.

As a result of investigations on the extracting reagent for separating a mixed fluid comprising HFC-125 and HFC-143a or for separating a mixed fluid comprising HFC-125, HFC-143a and CFC-115, the present inventors have accomplished the present invention.

SUMMARY OF THE INVENTION

It is therefore an object of the present invention to provide a process for efficiently separating a mixed fluid comprising HFC-125 and HFC-143a or a mixed fluid comprising HFC-125, HFC-143a and CFC-115.

The above objective has been achieved by providing a process for separating pentafluoroethane and 1,1,1-trifluoroethane, which comprises extraction distilling a mixed fluid comprising pentafluoroethane and 1,1,1-trifluoroethane in the presence of at least one extracting agent selected from the group consisting of esters and ketones each having a standard boiling point of from −10° C. to 100° C.

The above object of the present invention has also been achieved by providing a process for separating pentafluoroethane, 1,1,1-trifluoroethane and chloropentafluoroethane, which comprises extraction distilling a mixed fluid comprising pentafluoroethane, 1,1,1-trifluoroethane and chloropentafluoroethane in the presence of at least one extracting agent selected form the group consisting of esters and ketones each having a standard boiling point of from −10° C. to 100° C.

DESCRIPTION OF THE PREFERRED EMBODIMENTS

The present inventors have found an effective extracting reagent in an extraction distillation method for separating a mixed fluid comprising HFC-125 and HFC-143a or a mixed fluid comprising HFC-125, HFC-143a and CFC-115, which mixed fluids are very difficult to separate using a common distillation method.

The extracting reagent comprises at least one selected from esters and ketones each having a standard boiling point of from −10° C. to 100° C. Also provided is a process for separating a mixed fluid comprising HFC-125 and HFC-143a or a mixed fluid comprising HFC-125, HFC-143a and CFC-115 by an extraction distillation method using the above extracting reagent.

It has been found that when a mixed fluid comprising HFC-125 and HFC-143a or a mixed fluid comprising HFC-125, HFC-143a and CFC-115 is extraction distilled using at least one extracting agent selected from esters and ketones each having a standard boiling point of from −10° C. to 100° C., the mixed fluid is efficiently separated.

The extracting reagent is preferably selected from the group consisting of ethyl formate, methyl acetate, ethyl acetate, acetone and methyl ethyl ketone.

Due to the presence of the extracting reagent in the extraction distillation system, the specific volatility of HFC-143a or CFC-115 to HFC-125 shifts towards a value of greater than 1 to thereby obtain the above described separating effect.

In general, when the specific volatility is 1, the compositions of both the vapor and liquid phases become the same and separation by distillation is impossible.

For example, when the specific volatility of HFC-143a to HFC-125 becomes larger than 1, the molar fraction of HFC-143a in the vapor phase becomes larger than its molar fraction in the liquid phase. As a result, HFC-143a is concentrated in the vapor phase side, such that separation by distillation can be achieved.

Preferred extracting reagent for use in the present invention have the following standard boiling points:

ethyl formate 54° C.
methyl acetate 57° C.
ethyl acetate 77° C.
acetone 56° C.
ethyl methyl ketone 79° C.

As shown above, the boiling points of the preferred extracting reagents for use in the present invention are considerably higher than the boiling points of HFC-125, HFC-143a and CFC-115.

The difference in boiling point between the mixed fluid and the extracting reagent in general is about 30° C. or more, preferably 40° C. or more, in order to facilitate recovery of the extracting reagent.

Esters and ketones used as the extracting reagent of the present invention have a relatively high boiling point and preferably satisfy the above-described requirement.

These extracting reagents are inexpensive and commercially available, and are therefore highly practical for industrial use.

The extraction distillation method which is preferably used in the present invention comprises supplying an extracting reagent to a plate in the distillation tower higher than the raw material feed plate.

The type of distillation tower is not particularly limited as long as it is equipped with the functions needed for normal distillation, however, a superfraction tower such as packed tower or plate tower is preferred.

The operationing conditions for distillation are not particularly limited, and may vary depending on the utility or separation rate.

In order to prevent too much of a reduction in temperature at the top of the distillation tower, the operating pressure is preferably about 5 kg/cm$^2$abs or more.

In this case, the top temperature of the distillation tower is about −10° C. or higher.

In the distillation, because the specific volatility of HFC-143a to HFC-125 is changed to a value of greater than 1 by use of the extracting reagent of the present invention, a mixed fluid with HFC-125 containing a larger amount of HFC-143a as compared with the supply raw material distills from the top. Also, a mixed fluid of HFC-143a and the extracting reagent containing a larger amount of HFC-125 is obtained from the bottom.

By varying the conditions of the distillation operation, such as the amount of mixed fluid or extracting reagent that is supplied, the operating temperature, the operating pressure, the reflux ratio, the distillation amount or the bottom amount, HFC-143a substantially free of HFC-125 may be distilled from the top, or a mixed fluid of HFC-125 and the extracting reagent substantially free of HFC-143a may be obtained from the bottom.

Furthermore, the mixed fluid comprising HFC-125 and HFC-143a that is distilled or obtained from the bottom may be subjected to extraction distillation in a separate distillation tower using the same extracting reagent.

From the mixed fluid comprising HFC-125 and the extracting reagent or mixed fluid comprising HFC-125, HFC-143a and the extracting reagent obtained from the bottom of the distillation tower, only HFC-125 or HFC-143a is easily isolated by normal distillation. This is because the standard boiling point of the extracting reagent is high as compared to the standard boiling point of HFC-125 or HFC-143a.

On the other hand, the present inventors have found that the effect of the extracting reagent of the present invention on the mixed fluid comprising HFC-125, HFC-143a and CFC-115 is the same as the effect on a mixed fluid comprising HFC-125 and HFC-143a of the present invention and on a mixed fluid comprising HFC-125and CFC-115 as described by the present inventors in JP-A-7-133240. More specifically, the specific volatility of HFC-143a or CFC-115 to HFC-125 can be made greater than 1 by using the extracting reagent of the present invention.

When a mixed fluid comprising HFC-125, HFC-143a and CFC-115 is used as the raw material supply for the extraction distillation, depending on the specific volatilities of the respective constituent components, a mixed fluid of HFC-143a and CFC-115 containing a smaller amount of HFC-125 as compared with the raw material supply distills from the top. Also, a mixed fluid of HFC-143a, CFC-115 and the extracting reagent containing a larger amount of HFC-125 as compared with the raw material supply is obtained from the bottom.

By varying the conditions of the distillation operation, such as the amount of the mixed fluid or extracting reagent that is supplied, the operating temperature, the operating pressure, the reflux ratio, the distillation amount or the bottom amount, HFC-143a and CFC-115 substantially free of HFC-125 may be distilled from the top, or a mixed fluid of HFC-125 and the extracting reagent substantially free of HFC-143a CFC-115 may be obtained from the bottom.

Furthermore, a mixed fluid comprising HFC-125, HFC-143a and CFC-115 distilled or obtained from the bottom may be subjected to another extraction distillation using the same extracting reagent to obtain HFC-125 or HFC-143a in higher purity.

The extracting reagent in the mixed fluid obtained from the bottom of the distillation tower can be easily isolated from the mixed fluid by a normal distillation technique as described above.

The extracting reagent thus isolated may be recycled for repeated use in the extraction distillation.

In general, as the extracting reagent concentration is increased, the relative specific volatility of the substances to be separated is advantageously changed to a value that is farther from 1. In the present invention, the extracting reagent concentration is 20 wt % or more, preferably from 50 to 90 wt %.

The above-described extracting reagents may be used individually or may be used in combination of two or more thereof.

EXAMPLES

The present invention is described in greater detail by reference to the following Examples, however, the present invention should not be construed as being limited thereto.

Example 1

Into an Othmer-type vapor-liquid equilibrium measuring apparatus made of stainless steel, HFC-125 containing 5 wt % of HFC-143a was charged as a raw material. Thereto, ethyl formate, methyl acetate, ethyl acetate, acetone or methyl ethyl ketone was added as an extracting reagent, and the vapor-liquid equilibrium relationships were measured.

The results of the above series of tests are shown in Table 1.

TABLE 1

| Extracting Reagent | (Standard Boiling Point ° C.) | Extracting Reagent Concentration in Liquid Phase (wt %) | Specific Volatility of HFC-143a to HFC-125 |
|---|---|---|---|
| esters | | | |
| ethyl formate | (54) | 82 | 1.41 |
| methyl acetate | (57) | 81 | 1.40 |
| ethyl acetate | (77) | 70 | 1.35 |
| ketones | | | |
| acetone | (56) | 81 | 1.88 |
| methyl ethyl ketone | (79) | 86 | 1.64 |

With the use of any of the above extracting reagents, the specific volatility of HFC-143a to HFC-125 became greater than 1.

Example 2

Into an Othmer-type vapor-liquid equilibrium measuring apparatus made of stainless steel, HFC-125 containing 5 wt % of HFC-143a was charged as a raw material. Thereto, acetone was added as an extracting reagent to various predetermined concentrations and the vapor-liquid equilibrium relationships were measured.

The test results are shown in Table 2 below.

TABLE 2

| Acetone Concentration in Liquid Phase (wt %) | Specific Volatility of HFC-143a to HFC-125 |
|---|---|
| 19.6 | 1.38 |
| 41.9 | 1.52 |
| 61.1 | 1.69 |
| 80.1 | 1.88 |

The above results show that the specific volatility of HFC-143a to HFC-125 became larger and that the separation capability was further improved as the extraction reagent concentration in the liquid phase was increased.

Example 3

A superfraction tower made of stainless steel having a diameter of 65 mm and a theoretical plate number of 24 was used. HFC-125 containing 1 wt % of HFC-143a was fed to the 21st plate from the top as a raw material under a pressure of 6 kg/cm²abs at a rate of 2 kg/h. Acetone was fed to the 5th plate from the top as an extracting reagent at a rate of 4 kg/h.

Extraction distillation was performed at a reflux ratio of 2. As a result, a distillate was distilled off from the top at a rate of 0.12 kg/h, and a bottom product was obtained from the bottom at a rate of 5.88 kg/h.

The results obtained are shown in Table 3.

TABLE 3

| | Raw Material Supply | Extracting Reagent Supply | Distillate | Bottom Product |
|---|---|---|---|---|
| Flow Rate (kg/h) | 2.0 | 4.0 | 0.12 | 5.88 |
| Composition (wt %) | | | | |
| HFC-125 | 99.0 | | 83.34 | 31.97 |
| HFC-143a | 1.0 | | 16.66 | nd |
| acetone | | 100 | | 68.03 |

In this Example, the sensitivity limit of HFC-143a was 1 wt ppm. As used herein, "nd" means not detected.

The above results show that by subjecting HFC-125 having a purity of 99 wt % to extraction distillation, HFC-125 substantially free of HFC-143a was obtained as a bottom product.

Furthermore, when the bottom product was subjected to common distillation in a second distillation tower, high-purity HFC-125 containing 1 ppm or less of HFC-143a was obtained from the top.

The recovery of HFC-125 was about 95%.

Example 4

Using the same distillation tower as in Example 3, HFC-125 containing 5 wt % of HFC-143a and 1 wt % of CFC-115 was fed as a raw material to the 21st plate from the top under a pressure of 6 kg/cm²abs at a rate of 2 kg/h. Acetone was fed as an extracting reagent to the 5th plate from the top at a rate of 8 kg/h.

Extraction distillation was performed at a reflux ratio of 3. As a result, a distillate was removed at a rate of 0.31 kg/h from the top, and a bottom product was obtained at a rate of 9.68 kg/h from the bottom.

The results obtained are shown in Table 4.

TABLE 4

| | Raw Material Supply | Extracting Reagent Supply | Distillate | Bottom Product |
|---|---|---|---|---|
| Flow Rate (kg/h) | 2.0 | 4.0 | 0.31 | 9.68 |
| Composition (wt %) | | | | |
| HFC-125 | 94.0 | | 62.50 | 17.36 |
| HFC-143a | 5.0 | | 31.25 | nd |
| CFC-115 | 1.0 | | 6.25 | nd |
| acetone | | 100 | | 82.64 |

In this Example, the sensitivity limit of CFC-115 was 1 wt ppm.

The above results show that when HFC-125 having a purity of 94 wt % was subjected to extraction distillation, HFC-125 substantially free of HFC-143a and CFC-115 was obtained as a bottom product.

Similar to HFC-143a, CFC-115 is a substance which forms an azeotropic with HFC-125, and is known to be difficult to separate using a common distillation operation.

However, the present inventors verified from the above results that the presence of CFC-115 has no effect on the extraction distillation, and that CFC-115 can be separated simultaneously with HFC-143a from HFC-125.

When the bottom product was further subjected to common distillation in a second distillation tower, high-purity HFC-125 containing 1 ppm or less of each of HFC-143a and CFC-115 was obtained from the top.

The recovery of HFC-125 was about 90%.

As described above, the present invention provides a process for separating a mixed fluid having an azeotropic composition that is difficult to separate into its constituent components using a common distillation operation, such as a mixed fluid comprising pentafluoroethane and 1,1,1-trifluoroethane or a mixed fluid comprising pentafluoroethane, 1,1,1-trifluoroethane and chloropentafluoroethane. More particularly, the inventive process comprises extraction distilling in the presence of an extracting agent selected from readily available esters and ketones each having a standard boiling point of from −10° C. to 100° C.

While the invention has been described in detail and with reference to specific embodiments thereof, it will be apparent to one skilled in the art that various changes and modifications can be made therein without departing from the spirit and scope thereof.

What is claimed is:

1. A process for separating pentafluoroethane and 1,1,1-trifluoroethane, which comprises extraction distilling a mixed fluid comprising pentafluoroethane and 1,1,1-trifluoroethane in the presence of at least one extracting agent selected from the group consisting of esters and ketones each having a standard boiling point of from −10° C. to 100° C.

2. The separation process as claimed in claim 1, wherein the extracting reagent is selected from the group consisting of ethyl formate, methyl acetate, ethyl acetate, acetone and methyl ethyl ketone.

3. The separation process as claimed in claim 1, which comprises separating 1,1,1-trifluoroethane from a mixed fluid comprising pentafluoroethane and 1,1,1-trifluoroethane to obtain high-purity pentafluoroethane.

4. The separation process as claimed in claim 1, which comprises separating wherein pentafluoroethane from a mixed fluid comprising pentafluoroethane and 1,1,1-trifluoroethane.

5. The separation process as claimed in claim 1, which comprises extraction distilling the mixed fluid in a plate distillation tower having a top and a bottom, supplying the mixed fluid to a first feed plate of the distillation tower, and supplying the extracting agent to a second feed plate positioned higher than the first feed plate to recover 1,1,1-trifluoroethane substantially free of pentafluoroethane from the top of the distillation tower, or a mixture of pentafluoroethane and the extracting agent substantially free of 1,1,1-trifluoroethane from the bottom of the distillation tower.

6. The separation process as claimed in claim 5, which comprises supplying the extracting agent at a rate of 20 wt % or more of the total feed rate.

7. The separation process as claimed in claim 1, which comprises extraction distilling the mixed fluid in a packed distillation tower, supplying the mixed fluid to a first feed inlet of the distillation tower, and supplying the extracting agent to a second feed inlet positioned higher than the first feed inlet to recover 1,1,1-trifluoroethane substantially free of pentafluoroethane from the top of the distillation tower, or a mixture of pentafluoroethane and the extracting agent substantilly free of 1,1,1-trifluoroethane from the bottom of the distillation tower.

8. The separation process as claimed in claim 7, which comprises supplying the extracting agent at a rate of 20 wt % or more of the total feed rate.

9. The separation process as claimed in claim 1, which comprises extraction distilling in a distillation tower at a pressure of 5 kg/cm$^2$ absolute or higher.

10. A process for separating pentafluoroethane, 1,1,1-trifluoroethane and chloropentafluoroethane, which comprises extracting distilling a mixed fluid comprising pentafluoroethane, 1,1,1-trifluoroethane and chloropentafluoroethane in the presence of at least one extracting agent selected from the group consisting of esters and ketones each having standard boiling point of from −10° C. and 100° C.

11. The separation process as claimed in claim 10, wherein the extracting reagent is selected from the group consisting of ethyl formate, methyl acetate, ethyl acetate, acetone and methyl ethyl ketone.

12. The separation process as claimed in claim 10, which comprises separating 1,1,1-trifluoroethane and chloropentafluoroethane from a mixed fluid comprising pentafluoroethane, 1,1,1-trifluoroethane and chloropentafluoroethane to obtain high-purity pentafluoroethane.

13. The separation process as claimed in claim 10, which comprises extraction distilling the mixed fluid in a plate distillation tower having a top and a bottom, supplying the mixed fluid to a first feed plate of the distillation tower, and supplying the extracting agent to a second feed plate positioned higher than the first feed plate to recover 1,1,1-trifluoroethane and chloropentafluoroethane substantially free of pentafluoroethane from the top of the distillation tower, or a mixture of pentafluoroethane and the extracting agent substantially free of 1,1,1-trifluoroethane and chloropentafluoroethane from the bottom of the distillation tower.

14. The separation process as claimed in claim 13, which comprises supplying the extracting agent at a rate of 20 wt % or more of the total feed rate.

15. The separation process as claimed in claim 10, which comprises extraction distilling the mixed fluid in a packed distillation tower, supplying the mixed fluid to a first feed inlet of the distillation tower, and supplying the extracting agent to a second feed inlet positioned higher than the first feed inlet to recover 1,1,1-trifluoroethane and chloropentafluoroethane substantially free of pentafluoroethane from the top of the distillation tower, or a mixture of pentafluoroethane and the extracting agent substantially free of 1,1,1-trifluoroethane and chloropentafluoroethane from the bottom of the distillation tower.

16. The separation process as claimed in claim 15, which comprises supplying the extracting agent at a rate of 20 wt % or more of the total feed rate.

17. The separation process as claimed in claim 10, which comprises extraction distilling in a distillation tower at a pressure of 5 kg/cm$^2$ absolute or higher.

18. A process for separating pentafluoroethane and 1,1,1-trifluoroethane, which comprises extraction distilling a mixed fluid comprising pentafluoroethane and 1,1,1-trifluoroethane in the presence of an extracting agent which increases the specific volatility of 1,1,1-trifluoroethane to pentafluoroethane when added to the mixed fluid.

19. A process for separating pentafluoroethane, 1,1,1-trifluoroethane and chloropentafluoroethane, which comprises extraction distilling a mixed fluid comprising pentafluoroethane, 1,1,1-trifluoroethane and chloropentafluoroethane in the presence of an extracting agent which increases the specific volatility of 1,1,1-trifluoroethane or chloropentafluoroethane to pentafluoroethane when added to the mixed fluid.

* * * * *